(12) United States Patent
Pecor et al.

(10) Patent No.: US 9,604,038 B2
(45) Date of Patent: Mar. 28, 2017

(54) INFLATION AND DEFLATION MECHANISMS FOR INFLATABLE MEDICAL DEVICES

(75) Inventors: Robert Pecor, Aliso Viejo, CA (US); Jason Kwok, Anaheim, CA (US); Mark Ashby, Laguna Niguel, CA (US)

(73) Assignee: ReShape Medical, Inc., San Clemente, CA (US)

(*) Notice: Subject to any disclaimer, the term of this patent is extended or adjusted under 35 U.S.C. 154(b) by 519 days.

(21) Appl. No.: 13/386,650

(22) PCT Filed: Jul. 23, 2010

(86) PCT No.: PCT/US2010/043134
§ 371 (c)(1),
(2), (4) Date: Apr. 3, 2012

(87) PCT Pub. No.: WO2011/011741
PCT Pub. Date: Jan. 27, 2011

(65) Prior Publication Data
US 2012/0191126 A1     Jul. 26, 2012

Related U.S. Application Data (60) Provisional application No. 61/228,031, filed on Jul. 23, 2009.

(51) Int. Cl.
*A61M 29/00* (2006.01)
*A61M 25/10* (2013.01)
(Continued)

(52) U.S. Cl.
CPC ....... *A61M 25/10184* (2013.11); *A61F 5/003* (2013.01); *A61M 25/10181* (2013.11);
(Continued)

(58) Field of Classification Search
CPC ...... A61F 5/0013; A61F 5/003; A61F 5/0036; A61F 5/004; A61F 5/0043; A61F 5/0053; A61F 5/0056; A61F 5/0073
(Continued)

(56) References Cited

U.S. PATENT DOCUMENTS

| 1,666,690 A | 4/1928 | Drevitson |
| 1,690,995 A | 11/1928 | Pratt |

(Continued)

FOREIGN PATENT DOCUMENTS

| CA | 2638988 | 5/2007 |
| DE | 8708978 U1 | 11/1987 |

(Continued)

OTHER PUBLICATIONS

European Supplementary Search Report; EP Application No. 10802918.2, Applicant: ReShape Medical, Inc., mailed Jun. 5, 2013, 6 pgs.

(Continued)

*Primary Examiner* — Ashley Fishback
(74) *Attorney, Agent, or Firm* — Perkins Coie LLP

(57) ABSTRACT

According to embodiments, disclosed is an inflation and deflation device for an inflatable medical device, comprising: an inflation tubing disposed between an access block and a roller configured to rotate about an axis of a roller head; wherein the inflation tubing provides fluid communication between a container and the inflatable medical device; wherein the access block and the roller are configured to restrict flow through the inflation tubing at the area of pressure between the roller and the access block; and wherein the rotation of the roller about the axis of the roller head is configured to transport a fluid within the inflation tubing.

19 Claims, 3 Drawing Sheets

(51) Int. Cl.
*A61F 5/00* (2006.01)
*A61M 29/02* (2006.01)
*F04B 13/00* (2006.01)
*F04B 43/12* (2006.01)

(52) U.S. Cl.
CPC .............. *A61M 29/02* (2013.01); *F04B 13/00* (2013.01); *F04B 43/1253* (2013.01); *F04B 43/1261* (2013.01); *A61M 25/1018* (2013.01); *A61M 2210/1053* (2013.01)

(58) Field of Classification Search
USPC ................................ 604/96.01; 606/191–196
See application file for complete search history.

(56) References Cited

U.S. PATENT DOCUMENTS

| | | |
|---|---|---|
| 2,493,326 A | 1/1950 | Trinder |
| 2,579,301 A | 12/1951 | Buntin |
| 3,131,867 A | 5/1964 | Miller et al. |
| 4,133,315 A | 1/1979 | Berman et al. |
| 4,198,983 A | 4/1980 | Becker et al. |
| 4,246,893 A | 1/1981 | Berson |
| 4,356,824 A | 11/1982 | Vazquez |
| 4,368,739 A | 1/1983 | Nelson |
| 4,416,267 A | 11/1983 | Garren et al. |
| 4,436,087 A | 3/1984 | Ouchi et al. |
| 4,465,072 A | 8/1984 | Taheri |
| 4,465,818 A | 8/1984 | Shirahata et al. |
| 4,485,805 A | 12/1984 | Foster, Jr. |
| 4,543,089 A | 9/1985 | Moss |
| 4,598,699 A | 7/1986 | Garren et al. |
| 4,694,827 A | 9/1987 | Weiner et al. |
| 4,723,547 A | 2/1988 | Kullas et al. |
| 4,899,747 A | 2/1990 | Garren et al. |
| 4,940,458 A | 7/1990 | Cohn |
| 5,073,347 A * | 12/1991 | Garren et al. ................. 422/501 |
| 5,084,061 A | 1/1992 | Gau et al. |
| 5,123,840 A | 6/1992 | Nates |
| 5,234,454 A | 8/1993 | Bangs |
| 5,259,399 A | 11/1993 | Brown |
| 5,263,934 A | 11/1993 | Haak |
| 5,273,536 A | 12/1993 | Savas |
| 5,318,530 A | 6/1994 | Nelson, Jr. |
| 5,334,187 A | 8/1994 | Fischell et al. |
| 5,431,173 A | 7/1995 | Chin et al. |
| 5,496,271 A | 3/1996 | Burton et al. |
| 5,516,812 A | 5/1996 | Chu et al. |
| 5,575,772 A | 11/1996 | Lennox |
| 5,639,810 A | 6/1997 | Smith et al. |
| 5,643,209 A | 7/1997 | Fugoso et al. |
| 5,730,722 A | 3/1998 | Wilk |
| 5,779,728 A | 7/1998 | Lunsford et al. |
| 5,857,991 A | 1/1999 | Grothoff et al. |
| 5,876,376 A | 3/1999 | Schwab et al. |
| 5,904,701 A | 5/1999 | Daneshvar |
| 5,938,669 A | 8/1999 | Klaiber et al. |
| 5,976,073 A | 11/1999 | Ouchi |
| 5,993,473 A | 11/1999 | Chan et al. |
| 5,997,503 A | 12/1999 | Willis et al. |
| 6,050,274 A | 4/2000 | Gelardi et al. |
| 6,149,621 A | 11/2000 | Makihara |
| 6,179,878 B1 | 1/2001 | Duerig et al. |
| 6,254,355 B1 | 7/2001 | Gharib |
| 6,276,567 B1 | 8/2001 | Diaz et al. |
| 6,280,411 B1 | 8/2001 | Lennox |
| 6,283,951 B1 | 9/2001 | Flaherty et al. |
| 6,423,058 B1 | 7/2002 | Edwards et al. |
| 6,427,089 B1 | 7/2002 | Knowlton |
| 6,454,785 B2 | 9/2002 | De Hoyos Garza |
| 6,524,234 B2 | 2/2003 | Ouchi |
| 6,535,764 B2 | 3/2003 | Imran et al. |
| 6,540,789 B1 | 4/2003 | Silverman et al. |
| 6,547,788 B1 | 4/2003 | Maguire et al. |
| 6,579,301 B1 | 6/2003 | Bales et al. |
| 6,592,552 B1 | 7/2003 | Schmidt |
| 6,613,018 B2 | 9/2003 | Bagga et al. |
| 6,613,037 B2 | 9/2003 | Khosravi et al. |
| 6,689,051 B2 | 2/2004 | Nakada |
| 6,706,010 B1 | 3/2004 | Miki et al. |
| 6,746,460 B2 | 6/2004 | Gannoe et al. |
| 6,826,428 B1 | 11/2004 | Chen et al. |
| 6,850,128 B2 | 2/2005 | Park |
| 6,866,627 B2 | 3/2005 | Nozue et al. |
| 6,866,657 B2 | 3/2005 | Shchervinsky |
| 6,869,431 B2 | 3/2005 | Maguire et al. |
| 6,890,300 B2 | 5/2005 | Lloyd et al. |
| 6,890,346 B2 | 5/2005 | Ganz et al. |
| 6,902,535 B2 | 6/2005 | Eberhart et al. |
| 6,923,754 B2 | 8/2005 | Lubock |
| 6,931,286 B2 | 8/2005 | Sigg et al. |
| 6,939,299 B1 | 9/2005 | Petersen et al. |
| 6,942,680 B2 | 9/2005 | Grayzel et al. |
| 6,958,052 B1 | 10/2005 | Charlton |
| 7,001,419 B2 | 2/2006 | DiCaprio et al. |
| 7,016,735 B2 | 3/2006 | Imran et al. |
| 7,020,531 B1 | 3/2006 | Colliou et al. |
| 7,033,373 B2 | 4/2006 | de la Torre et al. |
| 7,056,305 B2 | 6/2006 | Garza Alvarez |
| 7,076,305 B2 | 7/2006 | Imran et al. |
| 7,081,125 B2 | 7/2006 | Edwards et al. |
| 7,131,945 B2 | 11/2006 | Fink et al. |
| 7,483,746 B2 | 1/2009 | Lee et al. |
| 7,625,355 B2 | 12/2009 | Yu |
| 7,749,254 B2 | 7/2010 | Sobelman et al. |
| 7,828,749 B2 | 11/2010 | Douglas et al. |
| 7,829,572 B2 | 11/2010 | Didiuk et al. |
| 7,931,693 B2 | 4/2011 | Binmoeller et al. |
| 8,083,757 B2 | 12/2011 | Gannoe et al. |
| 8,556,925 B2 | 10/2013 | Makower et al. |
| 8,840,952 B2 | 9/2014 | Ashby et al. |
| 8,894,568 B2 | 11/2014 | Pecor et al. |
| 9,050,174 B2 | 6/2015 | Pecor et al. |
| 2001/0022988 A1 | 9/2001 | Schwarz et al. |
| 2001/0037127 A1 | 11/2001 | De Hoyos Garza |
| 2002/0055757 A1 | 5/2002 | Torre et al. |
| 2002/0107515 A1 | 8/2002 | Edwards et al. |
| 2002/0161388 A1 | 10/2002 | Samuels et al. |
| 2002/0173804 A1 | 11/2002 | Rousseau |
| 2003/0105800 A1 | 6/2003 | Cullen |
| 2003/0114878 A1 | 6/2003 | Diederich et al. |
| 2003/0171768 A1 | 9/2003 | McGhan |
| 2003/0187390 A1 | 10/2003 | Bates et al. |
| 2004/0044354 A1 | 3/2004 | Gannoe et al. |
| 2004/0059289 A1 | 3/2004 | Garza Alvarez |
| 2004/0059290 A1 | 3/2004 | Palasis |
| 2004/0073162 A1 | 4/2004 | Bleam et al. |
| 2004/0087902 A1 | 5/2004 | Richter |
| 2004/0093058 A1 | 5/2004 | Cottone et al. |
| 2004/0106899 A1 | 6/2004 | McMichael et al. |
| 2004/0116897 A1 | 6/2004 | Aboul-Hosn |
| 2004/0127915 A1 | 7/2004 | Fleenor et al. |
| 2004/0186502 A1 | 9/2004 | Sampson et al. |
| 2004/0220665 A1 | 11/2004 | Hossainy et al. |
| 2004/0236280 A1 | 11/2004 | Rice et al. |
| 2004/0236361 A1 | 11/2004 | Sakurai |
| 2004/0254600 A1 | 12/2004 | Zarbatany et al. |
| 2005/0027283 A1 | 2/2005 | Richard et al. |
| 2005/0027313 A1 | 2/2005 | Shaker |
| 2005/0038415 A1 | 2/2005 | Rohr et al. |
| 2005/0055039 A1 | 3/2005 | Burnett et al. |
| 2005/0059990 A1 | 3/2005 | Ayala et al. |
| 2005/0075624 A1 | 4/2005 | Miesel |
| 2005/0085792 A1 | 4/2005 | Gershowitz |
| 2005/0119674 A1 | 6/2005 | Gingras |
| 2005/0131442 A1 | 6/2005 | Yachia et al. |
| 2005/0143784 A1 | 6/2005 | Imran |
| 2005/0159769 A1 | 7/2005 | Alverdy |
| 2005/0177103 A1 | 8/2005 | Hunter et al. |
| 2005/0192615 A1 | 9/2005 | Torre et al. |
| 2005/0228504 A1 | 10/2005 | Demarais |
| 2005/0267595 A1 | 12/2005 | Chen et al. |
| 2005/0267596 A1 | 12/2005 | Chen et al. |
| 2005/0273060 A1 | 12/2005 | Levy et al. |

(56) References Cited

U.S. PATENT DOCUMENTS

| | | |
|---|---|---|
| 2006/0058829 A1 | 3/2006 | Sampson et al. |
| 2006/0142700 A1 | 6/2006 | Sobelman et al. |
| 2006/0178691 A1 | 8/2006 | Binmoeller |
| 2006/0184112 A1 | 8/2006 | Horn et al. |
| 2006/0259020 A1 | 11/2006 | Sharratt |
| 2006/0270906 A1 | 11/2006 | Matsuno et al. |
| 2007/0016262 A1 | 1/2007 | Gross et al. |
| 2007/0078476 A1 | 4/2007 | Hull et al. |
| 2007/0083224 A1 | 4/2007 | Hively |
| 2007/0093728 A1 | 4/2007 | Douglas et al. |
| 2007/0100367 A1 | 5/2007 | Quijano et al. |
| 2007/0100368 A1 | 5/2007 | Quijano et al. |
| 2007/0100369 A1 | 5/2007 | Cragg et al. |
| 2007/0118168 A1 | 5/2007 | Lointier et al. |
| 2007/0135829 A1 | 6/2007 | Paganon et al. |
| 2007/0142770 A1 | 6/2007 | Rioux et al. |
| 2007/0149994 A1 | 6/2007 | Sosnowski et al. |
| 2007/0173881 A1 | 7/2007 | Birk et al. |
| 2007/0233161 A1 | 10/2007 | Weller et al. |
| 2007/0250020 A1 | 10/2007 | Kim et al. |
| 2007/0265369 A1 | 11/2007 | Muratoglu et al. |
| 2007/0265598 A1 | 11/2007 | Karasik |
| 2007/0288033 A1 | 12/2007 | Murature et al. |
| 2008/0058887 A1 | 3/2008 | Griffin et al. |
| 2008/0082056 A1 | 4/2008 | Mauch et al. |
| 2008/0085887 A1 | 4/2008 | Didiuk et al. |
| 2008/0097513 A1 | 4/2008 | Kaji et al. |
| 2008/0119729 A1 | 5/2008 | Copa et al. |
| 2008/0172079 A1 | 7/2008 | Birk |
| 2008/0190363 A1 | 8/2008 | Chen et al. |
| 2008/0208135 A1 | 8/2008 | Annunziata et al. |
| 2008/0208241 A1 | 8/2008 | Weiner et al. |
| 2008/0233167 A1 | 9/2008 | Li et al. |
| 2008/0243071 A1 | 10/2008 | Quijano et al. |
| 2008/0243166 A1 | 10/2008 | Paganon et al. |
| 2008/0255601 A1 | 10/2008 | Birk |
| 2008/0312679 A1 | 12/2008 | Hardert et al. |
| 2008/0319471 A1 | 12/2008 | Sosnowski et al. |
| 2009/0048624 A1 | 2/2009 | Alverdy |
| 2009/0259236 A2 | 10/2009 | Burnett et al. |
| 2009/0275973 A1 | 11/2009 | Chen et al. |
| 2009/0287231 A1 | 11/2009 | Brooks et al. |
| 2010/0023047 A1 | 1/2010 | Simpson |
| 2010/0049224 A1 | 2/2010 | Vargas |
| 2010/0063530 A1 | 3/2010 | Valencon |
| 2010/0130998 A1 | 5/2010 | Alverdy |
| 2010/0174307 A1 | 7/2010 | Birk |
| 2010/0191270 A1 | 7/2010 | Garza Alvarez |
| 2010/0234853 A1 | 9/2010 | Pecor et al. |
| 2010/0243135 A1 | 9/2010 | Pepper et al. |
| 2010/0251837 A1 | 10/2010 | Bouasaysy et al. |
| 2011/0172767 A1 | 7/2011 | Rathi et al. |
| 2011/0178544 A1 | 7/2011 | Sosnowski et al. |
| 2011/0276076 A1 | 11/2011 | Paganon |
| 2011/0295300 A1 | 12/2011 | Verd et al. |
| 2012/0271336 A1 | 10/2012 | Hamman et al. |
| 2012/0271338 A1 | 10/2012 | Bouasaysy et al. |
| 2012/0289992 A1 | 11/2012 | Quijano et al. |
| 2013/0035710 A1 | 2/2013 | Bouasaysy et al. |
| 2013/0053880 A1 | 2/2013 | Bouasaysy et al. |
| 2013/0060274 A1 | 3/2013 | Bouasaysy et al. |
| 2013/0102876 A1 | 4/2013 | Limon et al. |
| 2013/0261654 A1 | 10/2013 | Bouasaysy et al. |
| 2013/0296914 A1 | 11/2013 | Quijano et al. |
| 2014/0031850 A1 | 1/2014 | Bouasaysy et al. |
| 2014/0257358 A1 | 9/2014 | Alverdy et al. |
| 2014/0371775 A1 | 12/2014 | Ashby et al. |
| 2015/0216529 A1 | 8/2015 | Kwok et al. |
| 2015/0238342 A1 | 8/2015 | Sosnowski et al. |
| 2015/0265811 A1 | 9/2015 | Pecor et al. |
| 2015/0366691 A1 | 12/2015 | Bouasaysy |
| 2016/0008156 A1 | 1/2016 | Pecor et al. |

FOREIGN PATENT DOCUMENTS

| | | |
|---|---|---|
| EP | 0103481 | 3/1984 |
| EP | 0457456 A1 | 11/1991 |
| EP | 0485903 A2 | 5/1992 |
| EP | 1781183 | 5/2007 |
| FR | 2862525 A1 | 5/2005 |
| FR | 2892297 A1 | 4/2007 |
| GB | 2090747 A | 7/1982 |
| GB | 2139902 A | 11/1984 |
| JP | S57168674 | 10/1982 |
| JP | S6415063 | 1/1989 |
| JP | H091872 | 4/1989 |
| JP | H08322943 | 12/1996 |
| JP | 2001128985 | 5/2001 |
| JP | 2006333888 | 12/2006 |
| JP | 2015154964 | 8/2015 |
| JP | 2016127954 | 7/2016 |
| WO | 8805671 A1 | 8/1988 |
| WO | 9000369 A1 | 1/1990 |
| WO | 9925418 A1 | 5/1999 |
| WO | WO-0141700 | 6/2001 |
| WO | WO-0166166 A2 | 9/2001 |
| WO | 0240081 A2 | 5/2002 |
| WO | 2005082296 A1 | 9/2005 |
| WO | 2005107641 A2 | 11/2005 |
| WO | 2005120363 A1 | 12/2005 |
| WO | WO-2006035446 A2 | 4/2006 |
| WO | WO-2006056944 A1 | 6/2006 |
| WO | WO-2006/128978 A1 | 12/2006 |
| WO | WO-2007027812 A2 | 3/2007 |
| WO | WO-2007053556 A1 | 5/2007 |
| WO | WO-2007053706 A1 | 5/2007 |
| WO | WO-2007053707 A1 | 5/2007 |
| WO | WO-2007075810 A1 | 7/2007 |
| WO | WO-2008042819 A2 | 4/2008 |
| WO | WO-2008121831 A1 | 10/2008 |
| WO | WO-2009055386 A2 | 4/2009 |
| WO | WO-2009112786 A2 | 9/2009 |
| WO | WO-2010048021 | 4/2010 |
| WO | WO-2010115161 A2 | 10/2010 |
| WO | WO-2011011629 A2 | 1/2011 |
| WO | WO-2011011741 A2 | 1/2011 |
| WO | WO-2011011743 A2 | 1/2011 |
| WO | WO-2011024077 A2 | 3/2011 |
| WO | WO-2011038270 A2 | 3/2011 |
| WO | WO-2011097637 A1 | 8/2011 |
| WO | WO-2011127205 A1 | 10/2011 |
| WO | WO2012048226 | 4/2012 |

OTHER PUBLICATIONS

European Supplementary Search Report; EP Application No. 10802994.3, Applicant: ReShape Medical, Inc., mailed Jun. 28, 2013, 8 pgs.

Extended European Search Report; Application No. EP11748141.6, Applicant: Reshape Medical, Inc., mailed Feb. 25, 2014, 6 pages.

Non-Final Office Action; U.S. Appl. No. 11/263,302; dated: Oct. 9, 2012, 6 pages.

Non-Final Office Action; U.S. Appl. No. 12/625,473; dated Jul. 12, 2012; 10 pages.

Non-Final Office Action; U.S. Appl. No. 12/753,751; dated Oct. 5, 2012, 8 pages.

Non-Final Office Action; U.S. Appl. No. 13/074,956; dated Oct. 1, 2012, 8pages.

Final Office Action; U.S. Appl. No. 11/694,536, Mailing Date Mar. 11, 2011, 13 pages.

Final Office Action; U.S. Appl. No. 11/768,152, Mailing Date Jan. 19, 2011, 13 pages.

International Search Report; International Application No. PCT/US2010/042948; Applicant: ReShape Medical, Inc., Mailing Date Apr. 1, 2011, 11 pages.

International Search Report; International Application No. PCT/US2010/043134; Applicant: ReShape Medical, Inc., Mailing Date Apr. 27, 2011, 12 pages.

(56) References Cited

OTHER PUBLICATIONS

International Search Report; International Application No. PCT/US2010/043136; Applicant: ReShape Medical, Inc., Mailing Date Apr. 12, 2011, 9 pages.
International Search Report; International Application No. PCT/US2010/050260; Applicant: ReShape Medical, Inc., Mailing Date: Jun. 17, 2011, 9 pages.
International Search Report; International Application No. PCT/US2011/026233; Applicant: ReShape Medical, Inc., Mailing Date Apr. 26, 2011, 9 pages.
International Search Report; International Application No. PCT/US2011/031463; Applicant: ReShape Medical, Inc., Mailing Date: Jun. 27, 2011, 10 pages.
International Search Report; International Application No. PCT/US2003/012782, Applicant: Applied Medical Resources Corporation, dated: Oct. 28, 2003, 7 pages.
International Search Report; International Application No. PCT/US2006/042336, Applicant: Abdominus, Inc., dated: Mar. 14, 2007, 9 pages.
International Search Report; International Application No. PCT/US2006/042710, Applicant: Abdominus, Inc. et al., dated: Mar. 15, 2007, 9 pages.
International Search Report; International Application No. PCT/US2006/042711, Applicant: Abdominus, Inc. et al, dated: Mar. 16, 2007, 9 pages.
International Search Report; International Application No. PCT/US2006/048647, Applicant: Abdominus, Inc. et al., dated: May 22, 2007, 12 pages.
International Search Report; International Application No. PCT/US2008/058677, Applicant: ReShape Medical et al., dated: Aug. 21, 2008, 12 pages.
International Search Report; International Application No. PCT/US2008/068058, Applicant: ReShape Medical, Inc. et al, dated: Nov. 19, 2008, 11 pages.
International Search Report; International Application No. PCT/US2010/029865, Applicant: ReShape Medical, Inc., dated: Jan. 5, 2011, 9 pages.
International Search Report; International Application No. PCT/US2011/024077; Applicant: ReShape Medical, Inc., dated: Apr. 6, 2011, 12 pages.
International Search Report; International Application No. PCT/US2011/024082; Applicant: ReShape Medical, Inc., dated: Apr. 6, 2011, 10 pages.
International Search Report; International Application No. PCT/US1155373, Applicant: Reshape Medical, Inc., dated: Jan. 20, 2012, 7 pages.
Living with the BIB: BioEnterics Intragastric Balloon Program: Patient Information; INAMED Health, dated 2004, 10 pages.
Non-Final Office Action; U.S. Appl. No. 11/694,536; dated: Oct. 26, 2011, 13 pages.
Non-Final Office Action; U.S. Appl. No. 12/625,473; dated Oct. 24, 2011, 18 pages.
ReShape Inflatable Gastric Ballon Going on Trial as Weight Loss Option, MedGadget: Internet Journal of Emerging Medical Technologies. Feb. 4, 2010, 5 pages.
Supplementary European Search Report for EP 03726447.0, mailed Mar. 1, 2006.
Wahlen CH et al. "The BioEnterics Intragastric Balloon: How to use it" Obesity Surgery 2001; 11:524-527.
Non-Final Office Action; U.S. Appl. No. 12/723,545, date Feb. 29, 2012, 10 pages.
Extended European Search Report; Application No. EP11766679.2, Applicant: Reshape Medical, Inc., mailed Dec. 12, 2013, 6 pages.
Final Office Action; U.S. Appl. No. 13/858,767, Mailing Date May 30, 2013, 12 pages.
Extended European Search Report; Application EP11740536.5, Applicant: ReShape Medical, Inc., mailed Jul. 3, 2014, 8 pages.
Extended European Search Report; Application EP11831683.5, Applicant: Reshape Medical, Inc., mailed Jul. 3, 2014, 8 pages.
Final Office Action; U.S. Appl. No. 13/556,032, mailed on Jan. 28, 2014, 8 pages.
Notice of Allowance; U.S. Appl. No. 12/753,803, dated May 13, 2014, 18 pages.
Ostrovsky, ReShape Inflatable Gastric Balloon going on Trial as Weight Loss Option; http://www.medgadgetcom/2010/02/reshape_inflatable_gastric_balloon_system_going_on_trial_as_weight_loss_option.html Feb. 4, 2010, retrieved on 02-10-2-13.
Canadian Office Action: Application No. CA 2680124, Applicant: Reshape Medical Corporation, mailed Nov. 4, 2014, 3 pages.
Canadian Office Action; Application No. 2,691,530, mailed Dec. 18, 2014, 4 pages.
Canadian Office Action; Application No. CA 2638163, Applicant: Reshape Medical Corporation, mailed Mar. 10, 2015, 4 pages.
Canadian Office Action; Application No. CA 2638988, Applicant Reshape Medical Corporation, mailed Dec. 22, 2014 3 pages.
Canadian Office Action; Application No. CA 2638988, Applicant Reshape Medical Corporation, mailed Mar. 6, 2014, 4 pages.
Canadian Office Action; Application No. CA 2638989, Applicant: Reshape Medical Corporation, mailed May 22, 2013 3 pages.
Canadian Office Action; Application No. CA 2640554, Applicant: Reshape Medical Corporation, mailed May 27, 2013, 2 pages.
Canadian Office Action; Application No. CA2484838, Applicant: Reshape Medical, Inc., mailed Nov. 13, 2009, 3 pages.
Canadian Office Action; Application No. CA2484838, Applicant: Reshape Medical, Inc., mailed Sep. 24, 2010, 3 pages.
Canadian Office Action; Application No. CA2638163, Applicant: Reshape Medical Corporation, mailed Jul. 17, 2013, 2 pages.
Canadian Office Action; Application No. CA2638988, Applicant: Reshape Medical Corporation, mailed May 28, 2013, 3 pages.
Canadian Office Action; Application No. CA2780085, Applicant: Reshape Medical, Inc., mailed Jul. 23, 2012, 2 pages.
European Examination Report; Application No. 03726447.0, Applicant: Applied Medical Resources Corporation: Oct. 26, 2007, 4 pages.
European Examination Report; Application No. EP108002918.2, Applicant: Reshape Medical Inc., mailed Dec. 17, 2014, 5 pages.
European Examination Report; Application No. EP10802994.3, Applicant: Reshape Medical Inc., mailed Dec. 18, 2014, 4 pages.
European Examination Report; Application No. 08771842.5, May 7, 2015, 5 pages.
European Supplementary Search Report; Application No. 08771842.5, Apr. 24, 2015, 3 pages.
Extended European Search Report; Application No. 08732989.2, Applicant: Reshape Medical, Inc., mailed Oct. 16, 2014, 7 pages.
Extended European Search Report; Application No. EP6827098.3, Applicant: Reshape Medical, Corporation, mailed on Aug. 25, 2014, 3 pages.
Extended European Search Report; Application No. EP6827313.5, Applicant: ReShape Medical Corporation, mailed Jul. 30, 2014, 5 pages.
Extended European Search Report; Application No. EP6827314.3, Applicant: ReShape Medical Corporation, mailed Aug. 1, 2014, 3 pages.
Extended European Search Report; Application No. EP6847847.8, Applicant ReShape Medical Corporation, mailed Aug. 14, 2014, 5 pages.
Japanese Final Office Action; Application No. JP2013-043712, mailed Nov. 15, 2013, 5 pages.
Japanese Office Action; Application No. 2013-142327, mailed May 29, 2014, 4 pages.
Japanese Office Action; Application No. 2013-532976; mailed Jun. 26, 2015, 4 pages.
Japanese Office Action; Application No. 2014-52972; mailed Feb. 25, 2015, 7 pages.
Japanese Office Action; Application No. JP2010-501261, mailed Sep. 7, 2012, 10 pages.
Japanese Office Action; Application No. JP2010-515040, mailed Jan. 7, 2013, 18 pages.
Japanese Office Action; Application No. JP2012-503759, mailed Mar. 24, 2014, 5 pages.
Japanese Office Action; Application No. JP2013-43712, mailed Jan. 8, 2015, 8 pages.

(56) References Cited

OTHER PUBLICATIONS

Japanese Office Action; Application. No. JP2013-043712, mailed Apr. 22, 2013, 5 pages.
Canadian 2nd Office Action Application No. CA 2680124, Applicant: Reshape Medical, Inc., mailed Jul. 9, 2015, 3 pages.
Canadian Office Action, Application No. CA 2638163, Applicant: Reshape Medical, Inc., mailed Dec. 8, 2015, 4 pages.
Cronin, Carmel G. et al., "Normal small bowel wall characteristics on MR enterography," European Journal of Radiology 74(2):207-211, Aug. 2010.
European Examination Report; Application No. EP06827313.5, Applicant: Reshape Medical Inc., mailed Jul. 13, 2015, 4 pages.
European Examination Report; Application No. EP06847847.8, Applicant: Reshape Medical Inc., mailed Jul. 13, 2015, 4 pages.
Final Office Action for Japanese Application No. 2014-52972, Applicant: ReShape Medical, Inc., mailed on Oct. 9, 2015, 8 pages.
Gray, Henry, Anatomy of the Human Body. Philadelphia: Lea & Febiger, 1918. Section XI Splanchnology, 2g. The Small Intestine. Bartleby.com, 2000. Web. URL: www.bartleby.com/107/248.html. Accessed: Oct. 26, 2015. 12 pages.
Partial Supplementary European Search Report for European Application No. 11740535.7, Applicant: ReShape Medical, Inc., mailed Oct. 20, 2015, 7 pages.
Chou, Chyuan et al., "Structural Effects On The Thermal Properties Of PDPS/PDMS Copolymers," Journal of Thermal Analysis, vol. 40, pp. 657-667, 1993.
European Search Report for European Application No. 11740535.7, Applicant: ReShape Medical, Inc., mailed Mar. 8, 2016, 14 pages.
Extended European Search Report; Application No. 15198773.2, Application ReShape Medical Corporation, mailed Jul. 15, 2016, 7 pages.
European Examination Report; Application No. 11766679.2, Applicant: Reshape Medical Inc., mailed Dec. 1, 2016, 4 pages.
European Examination Report; Application No. 11748141.6, Applicant: Reshape Medical Inc., mailed Dec. 8, 2016, 3 pages.

\* cited by examiner

INFLATION AND DEFLATION MECHANISMS FOR INFLATABLE MEDICAL DEVICES

RELATED APPLICATION

The present application is a U.S. National Phase application under 35 U.S.C. 371 of International Application Ser. No. PCT/US2010/043134, filed Jul 23, 2010, which claims the benefit of U.S. Provisional Patent Application Ser. No. 61/228,031, filed Jul. 23, 2009, the entire contents of which are incorporated by reference in their entireties.

This application incorporates by reference U.S. Pat. Pub. No. 2007/0100368, published May 3, 2007; U.S. Pat. Pub. No. 2007/0100369, published May 3, 2007; U.S. Pat. Pub. No. 2007/0149994, published Jun. 28, 2007; WIPO Pub. No. WO 2007/053556, published Oct. 5, 2007; WIPO Pub. No. WO 2007/053707, published Oct. 5, 2007; WIPO Pub. No. WO 2007/053706, published Oct. 5, 2007; and WIPO Pub. No. WO 2007/075810, published May 7, 2007; WIPO Pub. No. WO/2008/121831, published Oct. 9, 2008; WIPO Pub. No. WO/2009/002989, published Dec. 31, 2008; each as if fully set forth herein in its entirety.

BACKGROUND

This disclosure relates to deflation and inflation mechanisms, process, and systems for implantable medical devices. In particular, this disclosure relates to devices and methods for controlling inflation and deflation of inflatable gastric space fillers.

SUMMARY

According to embodiments, disclosed is a method of controlling inflation of an inflatable medical device, comprising: determining a target volume of a fluid to be transferred to a medical device; determining an initial mass of a container and initial fluid therein; transferring at least a portion of the fluid from the container to the medical device; measuring a resulting mass of the container and remaining fluid therein; calculating the volume of transferred fluid to the medical device; and if the volume of transferred fluid is substantially equal to the target volume, ending the transferring.

The method may further comprise transferring an excess amount of fluid from the container prior to transferring the fluid from the container to the medical device, whereby the container contains only the target volume of fluid.

The method may further comprise, if the volume of transferred fluid is less than the target volume, transferring more of the fluid from the container to the medical device. The method may further comprise, if the volume of transferred fluid is greater than the target volume, transferring fluid from the medical device to the container. The method may further comprise, if the volume of transferred fluid is greater than the target volume, ceasing the transferring.

Calculating the volume of transferred fluid to the medical device may comprise: subtracting the resulting mass of the container and the remaining fluid therein from the initial mass of the container and the initial fluid therein to determine the change in mass; dividing the change in mass by the density of the fluid. The initial mass of a container and fluid therein may be known and provided from a manufacturer. The target volume may be the desired amount of volume to fill the medical device.

The medical device may be an implantable, inflatable intragastric balloon system.

The method may further comprise sensing a back pressure corresponding to the inflation state of the inflatable medical device and a resistance to further inflation due to interactions between the inflatable medical device and the walls of the stomach; and ceasing the transferring if the sensed back pressure corresponds to a target inflation state.

Determining the volume of a fluid in a container may further comprise: determining the mass of the fluid in the container; and dividing the mass of the fluid by the density of the fluid. Determining the mass of the fluid in the container may further comprise: determining a mass of only the container; determining a combined mass of the fluid and the container; and subtracting the mass of only the container from the combined mass of the fluid and the container. Determining the initial mass of the container and initial fluid therein may further comprise filling the container to the target volume. Determining the mass of the fluid in the container may further comprise filling the container to the target volume, wherein the container has markings for measuring volume. Determining the mass of the fluid in the container may further comprise receiving the container from a provider, the container being provided with the target volume.

According to embodiments, disclosed is a method of controlling deflation of an inflatable medical device, comprising: determining a target volume of a fluid to be transferred from a medical device; determining an initial mass of a container and initial fluid therein; transferring at least a portion of fluid from the medical device to the container; measuring a resulting mass of the container and resulting fluid therein; calculating the volume of transferred fluid from the medical device; and if the volume of transferred fluid is substantially equal to the target volume, ending the transferring.

The method may further comprise, if the volume of transferred fluid is less than the target volume, transferring more of the fluid from the medical device to the container. The method may further comprise, if the volume of transferred fluid is greater than the target volume, transferring fluid from the container to the medical device. The method may further comprise, if the volume of transferred fluid is greater than the target volume, ceasing the transferring.

According to embodiments, disclosed is a system for inflating and deflating a medical device, comprising: a container with fluid therein; a medical device; a pump connecting the container to the medical device, the pump being programmed to determine an initial mass of a container and fluid therein; transfer at least a portion of the fluid to the medical device; measure a mass of the container and remaining fluid therein; calculate the volume of transferred fluid to the medical device; and if the volume of transferred fluid is substantially equal to a target volume, end the transferring.

The pump may be a roller pump, comprising: an inflation tubing disposed between an access block and a roller configured to rotate about an axis of a roller head; wherein the inflation tubing provides fluid communication between the container and the medical device; wherein the access block and the roller are configured to restrict flow through the inflation tubing at the area of pressure between the roller and the access block; and wherein the rotation of the roller about the axis of the roller head is configured to transport a fluid within the inflation tubing.

The access block and the roller may be selectively moveable relative to each other such that a selective amount of pressure is imposed upon the inflation tubing.

DRAWINGS

The above-mentioned features and objects of the present disclosure will become more apparent with reference to the following description taken in conjunction with the accompanying drawings wherein like reference numerals denote like elements and in which.

DETAILED DESCRIPTION

Various inflatable and variable-volume medical devices exist. Examples include medical devices for the treatment of obesity that entail a single or multiple balloon system to be implanted in the stomach. These balloons may be made of silicone or other bio-compatible substances and may be filled with a fluid, such as a saline solution, as part of the implantation process. After a clinically designated or otherwise desired implant period within the stomach, it is desirable to pierce the balloon wall or otherwise access the interior of the balloons so that the balloon contents can be evacuated, such as by aspiration.

Historically, such balloon systems may be inflated manually using a syringe and associated tubing. This method may be physically demanding, time consuming, and complicated with many steps for the user to perform, presenting an increased risk of complications with a prolonged inflation procedure. Also, this method is vulnerable to human error because the user must count multiple syringe injections to track the volume of fluid that had been transferred to the balloon system. According to embodiments, disclosed herein is a method and system to inflate balloon systems that is faster, does not require physical exertion, and accurately transfers the target volume of liquid to the balloon system.

Figure 1:
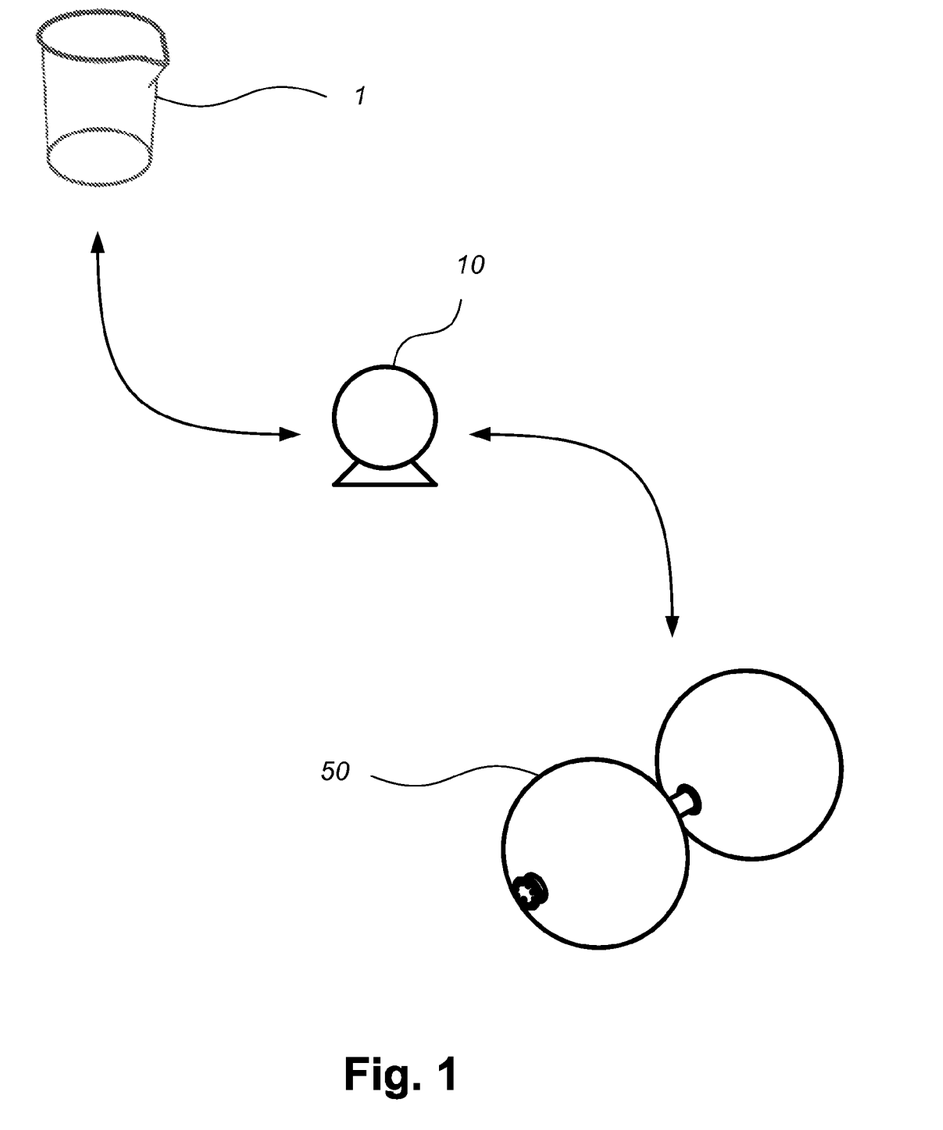
FIG. 1 shows connections between a container, a pump, and a medical device.

According to embodiments, and as shown in FIG. 1, container 1 capable of holding a fluid is provided in connection with pump 10 and inflatable medical device 50. Pump 10 is configured to transfer the fluid between the container and the inflatable medical device 50. Each of container 1, pump 10, and inflatable medical device 50 are connected by fluid-conducting tubing. Pump 10 may be manually operated or an automated machine.

Figure 2:
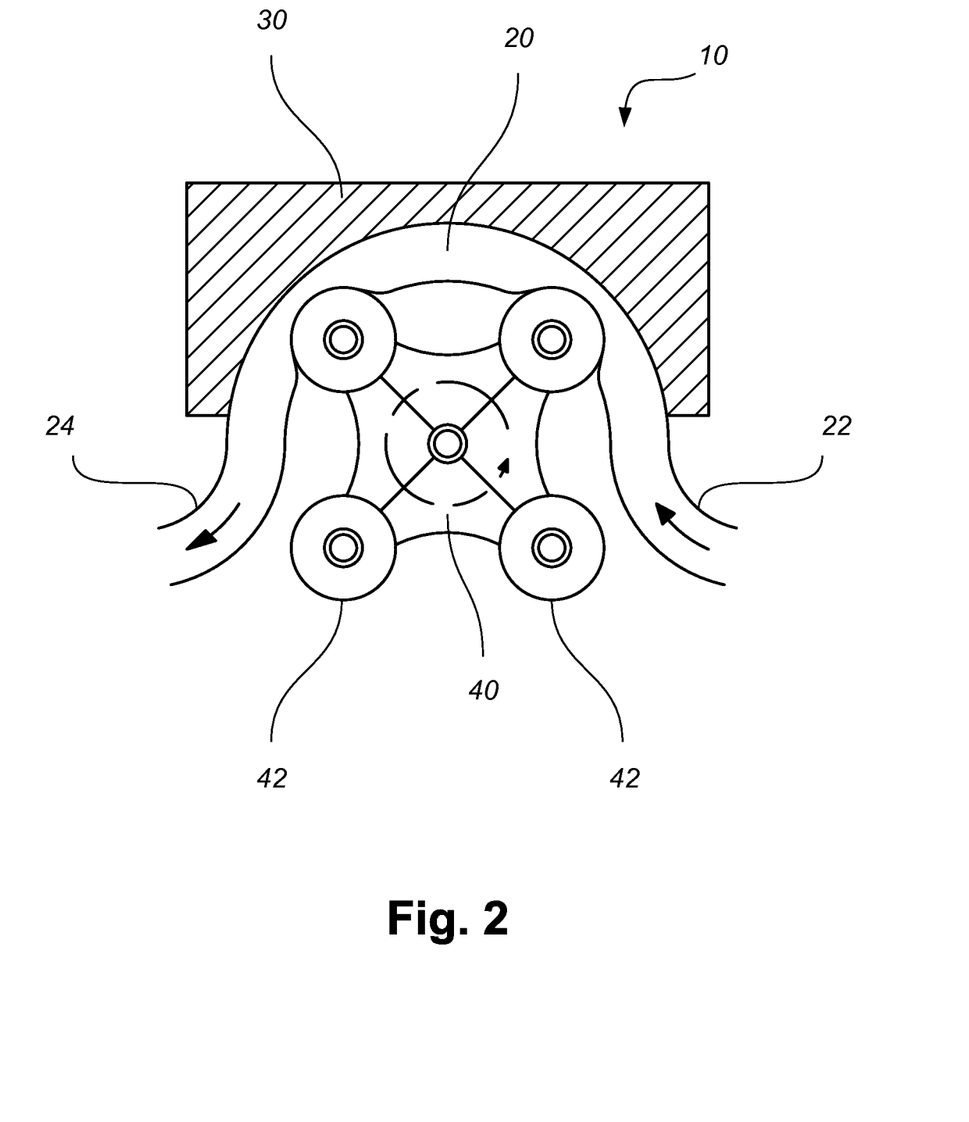
FIG. 2 shows a roller pump device.

According to embodiments, using a pump that allows easy access to load and unload inflation tubing is particularly advantageous. FIG. 2 shows an embodiment of pump 10 that provides easy access to load and unload inflation tubing 20. As illustrated, access block 30 is positioned in pump mode, such that with inflation tubing 20 positioned as shown, pump 10 acts to move fluid through inflation tubing 20 when roller head 40 rotates about an axis. Roller head 40 includes at least one roller 42 that extends from the axis and compresses inflation tubing 20 against access block 30 when access block 30 is in pump mode.

According to embodiments, other configurations are contemplated, including other ranges of motion for roller head 40 and accommodating geometries of access block 30 to provide compression of inflation tubing 20 as rollers 42 travel along the path of inflation tubing 20. When the user wants to load or unload inflation tubing 20, access block 30 may be lifted to an "open position." For example, a hinged access block 30 may facilitate easy access. Such a system allows the user to load and unload inflation tubing 20 in an axis transverse to the linear axis of inflation tubing 20. This is quick and does not risk contamination of the fluid path, as opposed to feeding the inflation tubing into the pump from a tubing end or attaching the inflation tubing to a pump with its own section of pump tubing.

According to embodiments, inflation tubing 20 includes first end 22 and second end 24. The direction of flow between first end 22 and second end 24 is controlled by the rotation of roller head 40, which may be reversed at will.

According to embodiments, a method of using pump 10 to aspirate fluid from inflatable medical device 50 prior to removal of inflatable medical device 50 is also disclosed. In one operation, with roller movement (e.g., roller head 40 rotation) as shown and the patient on second end 24 of pump 10, inflatable medical device 50 may be inflated by transferring a fluid from container 1 on first end 22 to inflatable medical device 50 on second end 24. By either switching the direction of roller movement (e.g., roller head 40 rotation) or by switching the location of container 1 to second end 24 and the location of inflatable medical device 50 to first end 22, deflation of inflatable medical device 50 may be accomplished, while filling container 1 with the fluid formerly present in inflatable medical device 50. Flow of the fluid in either direction may be monitored and controlled using the measurement and calculation methods disclosed herein.

According to embodiments, an example of a powered roller pump is the Klein Pump® by HK Surgical, San Clemente, Calif. Powered roller pumps provide reduced inflation time, accurately control the fluid volume, maintain the sterility of the fluid path, and do not require two hands for pumping or reciprocating action to repeatedly fill and evacuate a syringe or reservoir with the inflation fluid.

Other advantages of embodiments include reduced procedure time and personnel. For example, manual inflation rate is about 130 mL/min, compared to the pump inflation rates of about 350 mL/min. As a result, the user would save 3.4 minutes for an inflation volume of 700 cc and 4.4 minutes for 900 cc. The automated inflation also facilitates a single user inflation procedure, as the endoscopist can operate the pump via a remote switch, such as a foot switch, while maintaining control of the scope and observing the patient and monitor. This is different than using a reciprocating syringe technique, which necessitates a second operator and requires two hands for inflation.

According to embodiments, a method of measuring and calculating progress of an inflation or deflation method is disclosed herein. A user may select a container for a fluid (e.g. IV bag or bottle) for use during inflation of the balloon system.

The user may weigh or otherwise determine the mass of the container, $m_{container}$, without fluid. Then, the filled container is weighed to determine the total mass, $m_{total}$, including the mass of the container, $m_{container}$, and the mass of the fluid, $m_{fluid}$.

$$m_{total} = m_{container} + m_{fluid} \qquad \text{Eq. 1}$$

Expressed differently, the user may determine the mass of the inflation fluid by the measured total mass, $m_{total}$, and the known mass of the container, $m_{container}$:

$$m_{fluid} = m_{total} - m_{container} \qquad \text{Eq. 2}$$

Further, the volume of the fluid, $V_{fluid}$, may be determined by dividing the mass of the fluid, $m_{fluid}$, by the density of the fluid, $\rho_{fluid}$:

$$V_{fluid} = \frac{m_{fluid}}{\rho_{fluid}}. \qquad \text{Eq. 3}$$

The measurements and calculations performed thus far may be executed prior to connecting the container to a pump or to an inflatable medical device.

According to embodiments, the volume of fluid may be adjusted and verified by measurement and calculation such that the volume of fluid remaining in the container is the target amount to be transferred to an inflatable medical device.

A colorant, medication, or biocompatible sealant (such as mineral oil, silicone oil, or vegetable oil to improve the function of the balloon valves and/or to reduce the permeability of the balloon wall to the inflation fluid), may be mixed with the fluid before or after weighing at the discretion of the user. The user may drain excess fluid from the container using a pump or syringe.

According to embodiments, the above procedure of determining the volume of inflation fluid in the container is useful with aqueous fluid having a density equal or close to 1 g/mL. Also, the containers could be manufactured with the desired fluid volume to be provided to or with the target inflatable medical device.

According to embodiments, an inflation procedure may be performed with an initial volume of fluid, $V_{initial}$, followed by an evaluation operation. Where some volume of fluid, $V_{remaining}$, remains in the container, the volume transferred, $V_{transferred}$, may be determined. The volume remaining, $V_{remaining}$, and the volume transferred, $V_{transferred}$, are related by:

$$V_{initial} = V_{transferred} + V_{remaining}. \qquad \text{Eq. 4}$$

The volume remaining, $V_{remaining}$, is determinable by $$V_{remaining} = \frac{m_{remaining}}{\rho_{fluid}}, \qquad \text{Eq. 5}$$

where $m_{remaining}$, is the mass of the fluid remaining. The mass of the fluid remaining is measurable including the mass of the container, $m_{container}$. The mass of fluid transferred, $m_{transferred}$, is the difference of mass, $\Delta m$, of the container and contents between two points in time:

$$m_{transferred} = \Delta m = m_{fluid} - m_{remaining} \qquad \text{Eq. 6}$$

Thus, the volume transferred, $V_{transferred}$, may be expressed as:

$$V_{transferred} = \frac{\Delta m}{\rho_{fluid}} = \frac{m_{fluid} - m_{remaining}}{\rho_{fluid}}. \qquad \text{Eq. 7}$$

According to embodiments, the volume of fluid transferred to an inflatable medical device may be determined once, multiple times, at regular intervals, or in real-time. As used herein, "real-time" refers to processes that are performed on an ongoing basis, with output based on input values. "Real-time" considers and includes processes where output values are generated with at least nominal lag time from when input values are provided.

Figure 3:
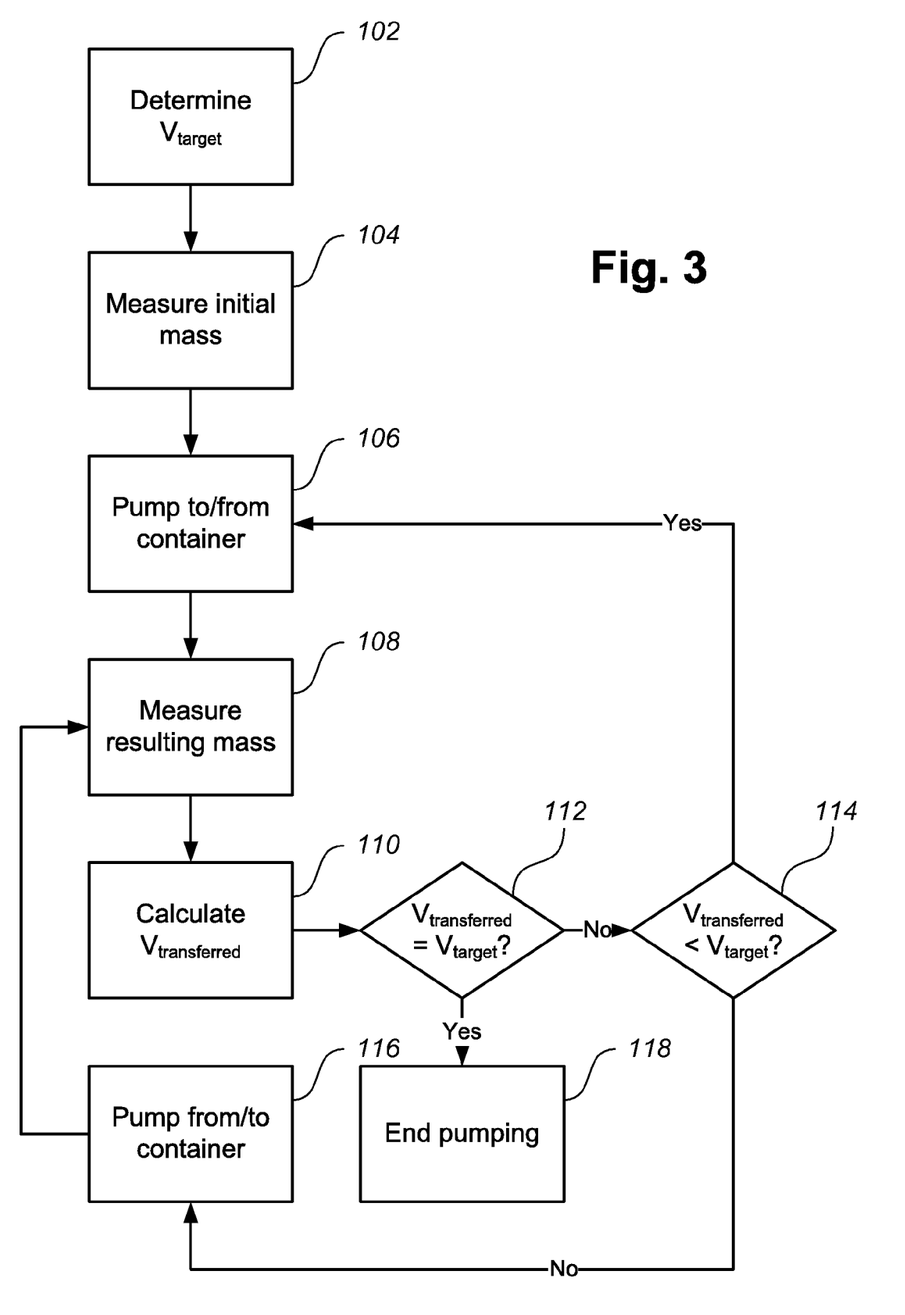
FIG. 3 shows a flow diagram of a method of inflating or deflation a medical device.

According to embodiments, the volume of fluid that had been infused into the balloon system can also be accurately measured during the inflation process. As shown in FIG. 3, operations may be sequentially performed to track volume into or out of an inflatable medical device. For example, in operation 102, a target volume, $V_{target}$, may be determined. $V_{target}$ may refer to a target volume to be transferred to or from an inflatable medical device. In operation 104, the initial mass of both the fluid and the container may be measured. In operation 106, a pump may operation to transfer fluid to or from the container and from or to the inflatable medical device. In operation 108, the resulting mass of both the fluid remaining and the container may be taken. In operation 110, the volume of fluid transferred may be calculated using the equations above. For example, this may be achieved by weighing the fluid container at the start and throughout the inflation process to track the loss in mass, and the volume of infused fluid can be calculated by dividing the lost mass by the density of the fluid.

In operation 112, the volume of fluid transferred may be compared to the target volume. If the target volume has been achieved, pumping may end in operation 118. Achievement of target volume may include being within an acceptable range of the target volume. The volume of fluid transferred is substantially equal to the target volume when it is within an acceptable range above or below the target volume. Acceptable ranges are those defined by a user or determined to be effective for a given purpose as demonstrated by knowledge of those having ordinary skill in the relevant art.

If the target volume has not been achieved, then the volume of fluid transferred may be further compared to determine whether it is greater than or less than the target volume, as in operation 114. If the volume of fluid transferred is less than the target volume, pumping may continue as in operation 106. Continuation of pumping may be the same as in previous execution(s) of operation 106 or modified based on the proximity of the volume of fluid transferred to the target volume (i.e., slower pumping as target is approached for greater precision).

If the target volume has been exceeded, then reverse pumping may be executed in operation 116, wherein pumping is in the opposite direction or having the opposite result as in operation 106. Subsequent comparisons to the target volume may be performed, as shown.

According to embodiments, accurate control of the inflation volume may also be achieved by transferring the fluid from bags or bottles to a container with a known volume or graduated markings that allow the user to measure out the volume of fluid to be transferred to the balloon system. Another advantage of such a method is that, in the case of the balloon system being partially filled, the user may determine the amount of fluid transferred to the balloon system using the graduated markings. Direct volume measurements may be primarily relied upon or be used as a backup or verification operation.

According to embodiments, accurate control of the inflation volume may also be achieved with the use of flow meters to track the volume of fluid that has been transferred into the balloon system. Direct flow rate measurements may be primarily relied upon or be used as a backup or verification operation. In both cases, there is continuous feedback of data on the volume of transferred fluid, which may be used to shut off or reverse a pump with a pre-programmed target inflation volume.

According to embodiments, a container of fluid can be provided with the target fluid volume before connecting the fluid source to the medical device. In this way, a user can preset the volume of the fluid source and eliminate risk of over-inflating or under-inflating the medical device.

According to embodiments, fluid can be transferred to a new container with volume markings before the inflation stage. Before the inflation stage, a user can fill the new container with fluid only up to the target inflation volume using the measuring and calculation methods disclosed herein. Thus, there is no risk of over-inflating or under-inflating the gastric balloon. Also, during the inflation stage, the user can use the markings to track how much fluid has been pumped to the gastric balloon.

According to embodiments, excess fluid may be transferred from an original container to a new container such that the original container contains the target volume. Such modifications to the original container may be performed according to the measuring and calculation methods disclosed herein, and such operations may be executed separate from and prior to connection to the medical device.

According to embodiments, a manufacturer can provide containers already filled with the target inflation volume, thereby bypassing such reliance on all of the steps required to determine the initial fluid volume. The user could simply pump the fluid from the container to the gastric balloon until the container is empty.

According to embodiments, devices and methods to monitor the balloon system during inflation to prevent inflating the balloon beyond what is tolerated by the stomach are disclosed. For example, this can be accomplished by connecting a manometer to the inflation tubing for continuous or intermittent pressure measurement. By further example, a manometer or pressure transducer in communication with the interior of the balloon may be attached to the inflation or placement portion of the balloon system. As the balloon fills the stomach and pushes against the stomach wall, the pressure within the balloon may increase at a rate different than when the balloon system is inflated without resistance. This difference in pressure rate may be used by the physician as an indication that the balloon system has reached the maximum tolerable size and the inflation process is complete. A "back pressure" corresponding to the resistance to further inflation may be present and increasing as the balloon system pushes against the stomach wall. This back pressure may be sensed as a function of pressure in the inflation tubing at or near a balloon, elsewhere in the fluid path, or as a function of the resistance to the movement path of a roller.

According to embodiments, sensing and response of such parameter and performance of any or all operations disclosed herein may be automated, performed manually, or a combination thereof. Where partially or fully automated, supporting hardware, software, and other devices and systems may be integrated or otherwise included to perform operations disclosed herein.

The process described above can be stored in a memory of a computer system as a set of instructions to be executed. In addition, the instructions to perform the processes described above could alternatively be stored on other forms of machine-readable media, including magnetic and optical disks and related media. For example the processes described could be stored on machine-readable media, such as magnetic disks or optical disks, which are accessible via a disk drive (or computer-readable medium drive). Further, the instructions can be downloaded into a computing device over a data network in a form of compiled and linked version.

Alternatively, the logic to perform the processes as discussed above could be implemented in additional computer or machine readable media, such as discrete hardware components as large-scale integrated circuits (LSI's), application-specific integrated circuits (ASIC's), firmware such as electrically erasable programmable read-only memory (EEPROM's); and electrical, optical, acoustical and other forms of propagated signals (e.g., carrier waves, infrared signals, digital signals, etc.).

According to embodiments, a kit of parts is disclosed, including components disclosed herein, for use by a user. Included in the kit may be instructions for use.

While the method and agent have been described in terms of what are presently considered to be the most practical and preferred embodiments, it is to be understood that the disclosure need not be limited to the disclosed embodiments. It is intended to cover various modifications and similar arrangements included within the spirit and scope of the claims, the scope of which should be accorded the broadest interpretation so as to encompass all such modifications and similar structures. The present disclosure includes any and all embodiments of the following claims.

It should also be understood that a variety of changes may be made without departing from the essence of the invention. Such changes are also implicitly included in the description. They still fall within the scope of this invention. It should be understood that this disclosure is intended to yield a patent covering numerous aspects of the invention both independently and as an overall system and in both method and apparatus modes.

Further, each of the various elements of the invention and claims may also be achieved in a variety of manners. This disclosure should be understood to encompass each such variation, be it a variation of an embodiment of any apparatus embodiment, a method or process embodiment, or even merely a variation of any element of these.

Particularly, it should be understood that as the disclosure relates to elements of the invention, the words for each element may be expressed by equivalent apparatus terms or method terms—even if only the function or result is the same.

Such equivalent, broader, or even more generic terms should be considered to be encompassed in the description of each element or action. Such terms can be substituted where desired to make explicit the implicitly broad coverage to which this invention is entitled.

It should be understood that all actions may be expressed as a means for taking that action or as an element which causes that action.

Similarly, each physical element disclosed should be understood to encompass a disclosure of the action which that physical element facilitates.

Any patents, publications, or other references mentioned in this application for patent are hereby incorporated by reference. In addition, as to each term used it should be understood that unless its utilization in this application is inconsistent with such interpretation, common dictionary definitions should be understood as incorporated for each term and all definitions, alternative terms, and synonyms such as contained in at least one of a standard technical dictionary recognized by artisans and the Random House Webster's Unabridged Dictionary, latest edition are hereby incorporated by reference.

Finally, all referenced listed in the Information Disclosure Statement or other information statement filed with the application are hereby appended and hereby incorporated by reference; however, as to each of the above, to the extent that such information or statements incorporated by reference might be considered inconsistent with the patenting of this/these invention(s), such statements are expressly not to be considered as made by the applicant(s).

In this regard it should be understood that for practical reasons and so as to avoid adding potentially hundreds of claims, the applicant has presented claims with initial dependencies only.

Support should be understood to exist to the degree required under new matter laws—including but not limited to United States Patent Law 35 USC 132 or other such laws—to permit the addition of any of the various dependencies or other elements presented under one independent claim or concept as dependencies or elements under any other independent claim or concept.

To the extent that insubstantial substitutes are made, to the extent that the applicant did not in fact draft any claim so as to literally encompass any particular embodiment, and to the extent otherwise applicable, the applicant should not be understood to have in any way intended to or actually relinquished such coverage as the applicant simply may not have been able to anticipate all eventualities; one skilled in the art, should not be reasonably expected to have drafted a claim that would have literally encompassed such alternative embodiments.

Further, the use of the transitional phrase "comprising" is used to maintain the "open-end" claims herein, according to traditional claim interpretation. Thus, unless the context requires otherwise, it should be understood that the term "compromise" or variations such as "comprises" or "comprising", are intended to imply the inclusion of a stated element or step or group of elements or steps but not the exclusion of any other element or step or group of elements or steps.

Such terms should be interpreted in their most expansive forms so as to afford the applicant the broadest coverage legally permissible.

The invention claimed is:

1. A method of controlling inflation of an inflatable medical device, comprising:
   determining a target volume of a fluid to be transferred to a medical device, wherein the medical device is an inflatable intragastric balloon system implanted within a stomach of a patient;
   determining an initial mass of a container and initial fluid therein;
   transferring at least a portion of the fluid from the container to the medical device;
   measuring a resulting mass of the container and remaining fluid therein;
   calculating the volume of transferred fluid to the medical device; and
   if the volume of transferred fluid is substantially equal to the target volume, ending the transferring.

2. The method of claim 1, further comprising:
   transferring an excess amount of fluid from the container prior to transferring the fluid from the container to the medical device, whereby the container contains only the target volume of fluid.

3. The method of claim 1, further comprising:
   if the volume of transferred fluid is less than the target volume, transferring more of the fluid from the container to the medical device.

4. The method of claim 1, further comprising:
   if the volume of transferred fluid is greater than the target volume, transferring fluid from the medical device to the container.

5. The method of claim 1, further comprising:
   if the volume of transferred fluid is greater than the target volume, ceasing the transferring.

6. The method of claim 1, wherein calculating the volume of transferred fluid to the medical device comprises:
   subtracting the resulting mass of the container and the remaining fluid therein from the initial mass of the container and the initial fluid therein to determine the change in mass;
   dividing the change in mass by the density of the fluid.

7. The method of claim 1, wherein the initial mass of a container and fluid therein is known and provided from a manufacturer.

8. The method of claim 1, wherein the target volume is the desired amount of volume to fill the medical device.

9. The method of claim 1, further comprising:
   sensing a back pressure corresponding to an inflation state of the inflatable medical device and a resistance to further inflation due to interactions between the inflatable medical device and walls of the stomach; and
   ceasing the transferring if the sensed back pressure corresponds to a target inflation state.

10. The method of claim 1, wherein determining the volume of a fluid in a container further comprises: determining a mass of the fluid in the container; and dividing the mass of the fluid by the density of the fluid.

11. The method of claim 10, wherein determining the mass of the fluid in the container further comprises:
    determining a mass of only the container;
    determining a combined mass of the fluid and the container; and
    subtracting the mass of only the container from the combined mass of the fluid and the container.

12. The method of claim 10, wherein determining the initial mass of the container and initial fluid therein further comprises:
    filling the container to the target volume.

13. The method of claim 10, wherein determining the mass of the fluid in the container further comprises:
    filling the container to the target volume, wherein the container has markings for measuring volume.

14. The method of claim 10, wherein determining the mass of the fluid in the container further comprises:
    receiving the container from a provider, the container being provided with the target volume.

15. The method of claim 1, further comprising filling the medical device with the fluid as part of an implantation process during a single inflation procedure.

16. A method of controlling deflation of an inflatable medical device, comprising:
    determining a target volume of a fluid to be transferred from a medical device, wherein the medical device is an inflatable intragastric balloon system implanted within a stomach of a patient;
    determining an initial mass of a container and initial fluid therein;
    transferring at least a portion of fluid from the medical device to the container;
    measuring a resulting mass of the container and resulting fluid therein;
    calculating the volume of transferred fluid from the medical device; and
    if the volume of transferred fluid is substantially equal to the target volume, ending the transferring.

17. The method of claim 16, further comprising:
    if the volume of transferred fluid is less than the target volume, transferring more of the fluid from the medical device to the container.

18. The method of claim 16, further comprising:
if the volume of transferred fluid is greater than the target volume, transferring fluid from the container to the medical device.

19. The method of claim 16, further comprising:
if the volume of transferred fluid is greater than the target volume, ceasing the transferring.

* * * * *